United States Patent [19]

Korant

[11] Patent Number: 4,675,387

[45] Date of Patent: Jun. 23, 1987

[54] METHOD FOR EXTRACTING PROTEIN WITH ORGANIC ACID

[75] Inventor: Bruce D. Korant, Wilmington, Del.

[73] Assignee: E. I. Du Pont de Nemours and Company, Wilmington, Del.

[21] Appl. No.: 759,180

[22] Filed: Jul. 26, 1985

[51] Int. Cl.$^4$ .............................................. C07K 3/20
[52] U.S. Cl. ...................................... 530/412; 530/422; 530/423; 530/351; 424/85; 435/68; 435/70
[58] Field of Search ..................... 260/112 R; 424/85; 435/68

[56] References Cited

U.S. PATENT DOCUMENTS 4,462,940 7/1984 Hanish ........................... 260/112 R
4,530,785 7/1985 Scharf ................................. 530/412

OTHER PUBLICATIONS

Itokura et al, "Expression in *E Coli* of a Chemically Synthesized Gene of the Harmone Somato Statin", Science, vol. 198, pp. 1056–1063, 1977.

*Primary Examiner*—John Kight
*Assistant Examiner*—Garnette D. Draper

[57] ABSTRACT

A method for extracting protein produced by procaryotic or eucaryotic cells comprising contacting said cells with a solution containing from about 50 to about 100 volume percent of an organic acid having from 1 to 5 carbon atoms and mixtures thereof is disclosed.

17 Claims, No Drawings

METHOD FOR EXTRACTING PROTEIN WITH ORGANIC ACID

FIELD OF THE INVENTION

This invention relates to a method for extracting protein produced by procaryotic or eucaryotic cells.

BACKGROUND OF THE INVENTION

Recombinant DNA techniques are currently being used to create genetically engineered cells capable of producing large quantities of a desired protein. It has been found that protein produced by genetically engineered cells can accumulate in an insoluble form which is difficult to extract by conventional techniques. A need exists for a commercially practical method capable of extracting this insoluble form of protein.

Fraenkel-Conrat, Virology, 4:1–4 (1957) discloses a method for degrading tobacco mosaic virus (TMV) with acetic acid. The reference discloses that cold 67% acetic acid splits TMV and causes precipitation of the nucleic acid from the solution. Two volumes of glacial acetic acid cooled to just above its freezing point are added to a cold virus solution. The resulting solution is cooled to about 3° C. and a precipitate appears, which is removed by centrifugation after 15 minutes. Native protein free from nucleic acid or other gross contaminants can be isolated from the supernatant by dialysis.

U.S. Pat. No. 4,364,863, issued to Leibowitz et al., discloses a method of extracting leucocyte and fibroblast interferons from interferon-expressing bacterial cells. The disclosed method comprises acidifying a suspension of interferon-containing bacterial cells, removing substantially all of the suspension liquid from the cells, preparing a second suspension of the acidified cells, neutralizing the second suspension, separating the interferon containing liquid from the suspended cells, and isolating the interferon from the liquid. The patent discloses that suitable acids are hydrochloric acid, nitric acid, sulfuric acid and phosphoric acid. The extraction is conducted at a temperature of from about ambient temperatures to about 40° C.

U.S. Pat. No. 4,405,601, issued to McEntire et al., discloses a method for the extraction and purification of biologically active lymphokines from large scale culture supernatants. The method comprises effecting the growth of lymphoblastoid cells from human lymphoblastoid cultured cell lines and thereafter harvesting, concentrating and clarifying the resulting supernatant culture fluids. The supernatant culture fluids are extracted with a solvent selected from the group consisting of trichloroacetic acid, guanidine hydrochloride, sodium dodecyl sulfate and perchloric acid and removing the solvent to produce a lymphokine fraction which exhibits the capability of inducing cell-mediated immunity reactions and tumor regression in mammals.

U.S. Pat. No. 4,450,103, issued to Konrad et al., discloses a process for recovering human IFN-beta (fibroblast interferon) from transformed bacteria. The process comprises disrupting the cell membranes of bacteria; solubilizing the IFN-beta from the disruptate into an aqueous medium with a solubilizing agent such as sodium dodecyl sulfate; extracting the IFN-beta from the aqueous medium with 2-butanol, 2-methyl-butanol, or mixtures thereof under conditions that maintain phase separation between aqueous medium and the extractant; and isolating the IFN-beta from the extractant such as by precipitating the IFN-beta from an aqueous buffer mixture of the extractant by lowering the pH thereof.

SUMMARY OF THE INVENTION

This invention provides a method for extracting protein produced by procaryotic or eucaryotic cells. The method comprises contacting the cells with a solution containing from about 50 to about 100 volume percent of an organic acid having from 1 to 5 carbon atoms and mixtures thereof at a temperature of from about 0° to about 40° C. to extract and solubilize protein present in the cells and recovering solubilized protein.

DETAILED DESCRIPTION OF THE INVENTION

The present invention provides a method for extracting protein produced by procaryotic or eucaryotic cells with an organic acid. No ionic detergents or other reagents are required. The method extracts protein in a soluble and nondenatured form which can be recovered by techniques known in the art.

As used herein the expression "transformed cell" means a procaryotic or eucaryotic cell that has been genetically engineered to produce a desired protein. Techniques for transforming cells and amplifying the expression of a desired gene are known in the art. It has been found that amplified production of a desired protein can result in the accumulation of the desired protein in an insoluble form which is difficult to extract by conventional techniques. The method of the present invention is especially useful for extracting and solublizing this insoluble form of protein.

In the method of the present invention procaryotic or eucaryotic cells are contacted with a solution containing from about 50 to about 100 volume percent of an organic acid having from 1 to 5 carbon atoms and mixtures thereof at a temperature of from about 0° to about 40° C. The solution containing the specified amount of organic acid can be contacted directly with intact cells or with cells having disrupted cellular membranes. Techniques for disrupting cellular membranes, like lysozyme digestion, sonication, or a combination thereof, are known in the art. It has been found that about one mL of solution containing the specified amount of organic acid can extract protein from about $1 \times 10^8 - 10^9$ cells.

The method of the present invention can be conducted in batch mode, continuous mode, or a combination thereof. In one embodiment of the present invention, a volume of cell suspension is mixed with about two volumes of organic acid to form a solution containing about 50 to about 100 volume percent organic acid. In another embodiment, a cell pellet is mixed with a solution containing the specified amount of organic acid. Preferably, the cells are contacted with a solution containing about 60 to about 80 volume percent organic acid and most preferably from about 65 to 70 volume percent. Timing is not critical, but preferably, the cells are contacted with a solution containing organic acid for about 30 minutes to about 17 hours, and most preferably from about 50 to about 70 minutes. In the resulting mixture soluble and insoluble materials separate into two layers. Solubilized protein present in the mixture is recovered by techniques known in the art, like precipitation, electrophoresis, molecular sieve chromatography, or affinity chromatography.

In the method of the present invention, protein produced by eucaryotic or procaryotic cells can be extracted. Preferably, the cells are procaryotic cells, and most preferably bacterial cells, such as transformed *E. coli* or transformed *B. subtilis*. Preferably, the extracted protein is a lymphokine, such as an interferon, or a lymphocyte modulator, such as interleukin-2.

In the method of the present invention protein is extracted without exposure to ionic detergent. Purification steps required when isolating protein extracted with ionic detergent, like electrodialysis, are not required in the method of the present invention. Protein denaturation caused by exposure to ionic detergent is thus eliminated. Preferably, the organic acid is selected from the group consisting of acetic acid, formic acid, propionic acid, butyric acid, isobutyric acid, and mixtures thereof. Most preferably, the organic acid is acetic acid. When subjected to isoelectric focusing, protein extracted in the method of the present invention with acetic acid produces sharper bands with greater separation than proteins extracted with sodium dodecyl sulfate (SDS). Protein extracted in the present method with acetic acid produces greater resolution when subjected to high pressure liquid chromatography (HPLC) than proteins extracted with SDS. Since SDS must be removed from a protein sample before the sample can be applied to a HPLC column, the present method of extraction eliminates this removal step.

The method of the present invention is further described by the following examples, wherein parts and percentages are by volume and degrees are Celcius, unless otherwise stated. In the Examples, betainterferon (beta-IFN) activity was determined according to the following procedure. Interleukin-2 (IL-2) activity was determined according to a procedure similar to that described by Gillis et al., *J. Immunol.*, 120: 2027–2032 (1978).

Procedure for Analysis of Interferon Activity

An interferon containing sample is diluted in an assay medium having the following ingredients.
Eagles Minimum Essential Medium
11.5% Sodium Bicarbonate
0.1% Gentamicin
1% Fungizone
7% Fetal bovine serum
Eagles Minimum Essential Medium is a liquid broth medium which is known in the art and available commercially from Gibco Laboratories. Eight 1:2 serial dilutions of the sample having a volume of 0.2 mL, a virus control, and a cell control are prepared in a 96-well tissue culture cluster with flat bottom wells. Human diploid fibroblast cells are suspended in the assay medium at a concentration of between 2 and $4 \times 10^5$ cells per mL and 0.1 mL of the resulting cell suspension is added to each well. The resulting cultures are incubated at 37° for 4 to 5 hours in the presence of 5% $CO_2$. Vesicular Stomatitis Virus (VSV) (1 plaque-forming unit (one virus) per cell) is added to each well except those serving as cell controls and the resulting combinations are incubated for 40 hours at 37° in the presence of 5% $CO_2$. The medium is removed from the wells and the resulting residue is stained with a solution of 1% crystal violet and 20% ethanol in water. Wells in which virus replication occur are identified by cytopathological effect.

In the Examples, one unit of interferon activity per mL is the concentration of interferon that inhibits virus caused cytopathological effects by 50%.

Examples 1–2 and Comparative Experiment A
Extraction of Beta-IFN from Transformed *E. coli*

HB101 *E. coli* were transformed with plasmid pkGP13-19R-trp6, ATCC accession number 39412. The transformed *E. coli* were grown for 4 hours at 37° in 100 mL of minimal medium M-9 lacking tryptophan. Minimal medium M-9 is described in Maniatis et al., *Molecular Cloning, A Laboratory Manual*, Cold Spring Harbor Laboratory, p 68 (1982), the disclosure of which is incorporated herein by reference. Growth of the transformed *E. coli* in the minimal medium causes amplification of the plasmids and overproduction of beta-IFN product. The *E. coli* were harvested by centrifugation and the resulting cell pellet was frozen. The cell pellet was thawed and suspended in 10 mL of 0.05 M Tris and 0.01 M ethylenediaminetetraacetic acid (EDTA) buffer. The resulting cell suspension was separated into three equal samples designated A, B, and C.

EXAMPLE 1

Acetic Acid Extraction

One mL of Sample A was placed in a dialysis bag and dialyzed against 1000 volumes (1 L) of 67% acetic acid for 16 hours at 6° with constant stirring of the dialysate. The resultant dialysand was assayed for beta-IFN activity. The results are shown in Table I.

EXAMPLE 2

Acetic Acid Extraction

Two volumes (2 mL) of glacial acetic acid chilled to about 5° were added to one volume (1 mL) of Sample B. The resulting combination began to clear almost immediately, and within 10 minutes soluble and insoluble materials had separated into two distinct layers. The combination was placed in an ice bath for 17 hours and stirred occasionally by means of a vortex mixer. 0.01 mL aliquots were removed from the soluble layer of the combination after 1 minute, 10 minutes, 60 minutes, and 17 hours and assayed for beta-IFN activity. The results are shown in Table I.

Comparative Experiment A

SDS Extraction

Sodium docecyl sulfate (SDS) was added to 1 mL of Sample C to a final concentration of 1% (W/V) and the resulting combination was incubated at 37° for 60 minutes. Soluble and insoluble materials in the combination separated into two distinct layers. The soluble layer was assayed for beta-IFN activity and the results are shown in Table I.

TABLE I

| | | Beta-IFN Activity | |
|---|---|---|---|
| Ex- ample | Comp. Exper. | Extraction Method | Beta-IFN Activity (units/mL) |
| Control | | None | 160 |
| 1 | | Acetic Acid (67%, dialyzed, 17 hr) | <1,000 |
| 2 | | Acetic Acid (67%, 1 min) | 1,000 |
| 2 | | Acetic Acid (67%, 10 min) | 3,200 |
| 2 | | Acetic Acid (67%, 60 min) | 350,000 |
| 2 | | Acetic Acid (67%, 17 hr) | 700,000 |
| | A | SDS (1% (W/V), 60 min) | 350,000 |

Example 3 and Comparative Experiments B and C

Extraction of Beta-IFN from Transformed *E. coli*

HB101 *E. coli* were transformed and grown according to methods similar to those of Example 1. A 0.5 mL innoculum of the transformed *E. coli* was added to 5 mL of a liquid broth medium (Bacto tryptone (10 g/L), yeast extract (5 g/L), and NaCl (5 g/L)) which contained 100 ug/mL of ampicillin. The medium is available commercially from Bifco Company under the trade name Luria Broth. The resulting culture was incubated for about 16 hours at 33° with agitation at 250 RPM. Two 0.5 mL aliquots were removed from the culture. Each aliquot was added to 50 mL of minimal medium M-9, similar to that of Example 1, which contained 100 ug/mL of ampicillin. The resulting cultures were incubated at 37°, until both cultures had an optical density reading of 0.6 at a wavelength of 550 nm. The two cultures were mixed together and two 25 mL samples of the resulting cell suspension, designated D and E, were removed for extraction with acetic acid and phosphoric acid, respectively, and a 1 mL sample of the cell suspension, designed F, was removed for extraction with SDS.

EXAMPLE 3

Acid Extraction

Sample D (25 mL) was chilled to 5° and centrifuged at 5,000×g for 10 minutes at 5°. The resulting supernatant was decanted and discarded. The resulting cell pellet was suspended in 5.0 mL of cold (5°) 50 mM Tris HCl buffer at pH 7.5 which contained 0.14 M NaCl. 10 mL of glacial acetic acid were added to the resulting cell suspension to form a combination with a pH of 1.22. The combination was gently mixed for 20 seconds, placed in an ice bath for one hour, and assayed for beta-IFN activity. The results are shown in Table II.

Comparative Experiment B

Phosphoric Acid Extraction

Phosphoric acid (85%) was added dropwise to Sample E (25 mL) to form a mixture with pH 2.1. The mixture was allowed to stand at ambient temperature for one hour with occasional stirring, and centrifuged at 5,000×g for 10 minutes. A sample of the resulting supernatant was removed for analysis of beta-IFN activity. The resulting cell pellet was suspended in 2.5 mL of 50 mM tris buffer at pH 7.5 which contained 0.15 M NaCl. The pH of the resulting suspension was raised to 7.3 by the addition of 3 N NaOH and the resulting combination was mixed for 1 hr at 4° and maintained at pH 7.3. The combination was centrifuged at 5,000×g for 10 minutes and the resulting supernatant was assayed for beta-IFN activity. The resulting pellet was suspended in 15 mL of 2×SGB solution which contained 2% SDS and 25% glycerol in 200 mM tris HCl at pH 6.5. The resulting suspension was heated in boiling water for 5 minutes, and assayed for beta-IFN activity. The results are shown in Table II.

Comparative Experiment C

SDS Extraction

Sample F (1 mL) was chilled to 5° and centrifuged at 5,000×g for 30 seconds. The resulting supernatant was decanted and discarded. The resulting cell pellet was suspended in 60 uL of 2×SGB solution which contained 2% SDS (W/V) and 25% glycerol in 200 mM tris HCl at pH 6.5. The resulting cell suspension was heated in boiling water for 5 minutes and assayed for beta-IFN activity. The results are shown in Table II.

TABLE II

| Example | Comp. Exper. | Extraction Method | Beta-IFN Activity (units/mL of culture) |
|---|---|---|---|
| 3 | | Acetic Acid (67%) | 1600 |
| | B | Phosphoric Acid Supernatant | <100 |
| | | SDS Extracted Pellet | 2560 |
| | C | SDS (2% (W/V)) | 3200 |

Example 4 and Comparative Experiment D

Isoelectric Focusing of Beta-IFN Extracted from Transformed *E Coli*

Isoelectric focusing conducted on beta-IFN extracted from transformed *E. coli*. HB101 *E. coli* were transformed, grown, harvested, and suspended according to methods similar to those of Example 1 to form Sample G.

EXAMPLE 4

Acetic Acid Extraction

Two volumes (2 mL) of glacial acetic acid were added to one volume (1 mL) of Sample G. The resulting combination was placed in an ice bath for 17 hours and stirred occasionally by means of a vortex mixer. Soluble and insoluble materials separated into two distinct layers. 40 uL of the soluble layer were loaded onto a slab gel of 5% polyacrylamide and subjected to isoelectric focusing according to a procedure similar to that described by Knight and Korant, *PNAS*, 76:1824 (1979), the disclosure of which is incorporated herein by reference. A portion of the resulting gel was stained with Coomassie Blue to visualize the extracted proteins. The unstained portion of the gel was cut in 1 cm slices which were eluted into 1 mL aliquots of water. Each aliquot was assayed for beta-IFN activity and the results are shown in Table III.

Comparative Experiment D

SDS Extraction

Sodium dodecyl sulfate was added to 1 mL of Sample G to a final concentration of 1% (W/V) and the resulting combination was incubated at 37° for 60 minutes. Soluble and insoluble material separated into two distinct layers. 40 uL of the soluble layer were subjected to isoelectric focusing according to a procedure similar to that of Example 4. A portion of the resulting gel was stained with Coomassie Blue to visualize the extracted proteins. The unstained portion of the gel was cut in 1 cm slices which were eluted into 1 mL aliquots of water. Each aliquot was assayed for beta-IFN activity and the results are shown in Table III.

TABLE III

| Example | Comp. Exper. | Extraction Method | Beta-IFN Activity (units/mL) |
|---|---|---|---|
| 4 | | Acetic Acid (67%) | 3000 |
| | D | SDS (1% (W/V)) | 1000 |

Isoelectric focusing of protein extracted by acetic acid produced sharper bands with greater resolution than protein extracted by SDS. Also, three times more beta-IFN activity was recovered after isoelectric focusing of the protein extracted with acetic acid than the protein extracted with SDS.

EXAMPLE 5

High Pressure Liquid Chromatography of Beta-IFN Extracted from Transformed *E. coli* with Acetic Acid High pressure liquid chromatography (HPLC) was conducted on beta-IFN extracted from transformed *E. coli*. HB101 *E. coli* were transformed and grown according to methods similar to those of Example 1. 40 mL of the resulting cell suspension were harvested by centrifugation. The resulting cell pellet was suspended in 10 mL of 0.05 M Tris and 0.01 M EDTA buffer at pH 7.8. The resulting cell suspension was recentrifuged and the resulting pellet was resuspended in two 2 mL aliquots of the same buffer. The resulting aliquots of cell suspension were extracted with acetic acid. One aliquot was extracted directly while the other aliquot was treated with lysozyme and sonication prior to extraction.

One aliquot of cell suspension was incubated with lysozyme (1 mg/mL) for 30 minutes at 0°, subjected to three bursts of sonication, each of ten seconds duration and centrifuged. The resulting pellet was suspended in 1 mL of 67% acetic acid for 1 hour at 37° and then diluted with water to a final acetic acid concentration of 20%.

Two volumes (4 mL) of glacial acetic acid were added to another aliquot (2 mL) of the cell suspension prepared above. The resulting combination was incubated for one hour at 37° and then diluted with water to a final acetic acid concentration of 20%.

The two resulting samples were separately subjected to high pressure liquid chromatography according to the following procedures. Each sample was charged to a Beckman RPSC reverse phase column (4.6×77 mm) which had been equilibrated with 5% formic acid at 35° and adjusted to a flow rate of 0.5 mL/min. A gradient solution of from 0 to 40% 1-propanol in 5% formic acid was used to elute bound protein from the column in 1 mL fractions. These fractions were assayed for beta-IFN activity and analyzed in SDS acrylamide gels for protein content. Beta-IFN was eluted from each sample in three fractions which were associated with a single peak of protein with an extinction coefficient at 280 nM. SDS gel electrophoresis indicated that the protein in the three fractions was about 95% homogeneous. The fraction containing the greatest amount of interferon activity was evaporated and re-chromatographed on the same column with a mobile phase of 0.1% trifluoroacetic acid and a gradient of 20 to 70% acetonitrile. The fractions which constituted the peak observed at 280 nM were analyzed for beta-IFN activity and protein content as before. These fractions were found to contain all of the interferon activity. The results are shown in Table IV.

TABLE IV

| | | Beta-IFN Activity | | |
|---|---|---|---|---|
| Example | Sample | Before** (units/mg) | After** and HPLC (units/mg) | After** Re-chromatography (units/mg) |
| 5 | Whole cells | 3 × 10⁵ | 2 × 10⁶ | 4 × 10⁵ |
| 5 | Cells treated w/lysozyme | 2 × 10⁵ | 9 × 10⁵ | 3 × 10⁶ |

TABLE IV-continued

| | | Beta-IFN Activity | | |
|---|---|---|---|---|
| Example | Sample | Before** (units/mg) | After** and HPLC (units/mg) | After** Re-chromatography (units/mg) |
| | and sonicated | | | |

**Acetic Acid Extraction

EXAMPLES 6-7 and Comparative Experiments E and F Extraction of IL-2 from Transformed *E. Coli*

MM294 *E. coli* were transformed with plasmid pTrpEIL-2, ATCC accession number 39750. The transformed *E. coli* were grown for 6 hours at 37° in 2 L of a liquid broth medium similar to that described in Example 3 which contained 100 ug/mL of ampicillin. Four 12.5 mL aliquots of the resulting cultures were separately harvested by centrifugation, suspended in 10 mL of 0.05 M Tris and 0.01 M EDTA buffer, centrifuged and resuspended in 1 mL of the same buffer. The four resulting samples were designated H, I, J, and K.

EXAMPLE 6

Acetic Acid Extraction

Sample H (1 mL) was centrifuged and the resulting cell pellet was suspended in 0.5 mL of 67% acetic acid. The resulting combination was incubated for 1 hour at 40° and centrifuged. The resulting supernatant was assayed for IL-2 activity. The results are shown in Table V.

Comparative Experiment E

SDS Extraction

Sample I (1 mL) was centrifuged and the resulting cell pellet was suspended in 0.5 mL of 1% SDS. The resulting mixture was incubated for 1 hour at 40° and centrifuged. The resulting supernatant was assayed for IL-2 activity. The results are shown in Table V.

EXAMPLE 7

Acetic Acid Extraction

Sample J (1 mL) was sonicated three times, each for 10 sec. The resulting suspension was centrifuged and the resulting cell pellet was suspended in 0.5 mL of 67% acetic acid. The resulting combination was incubated for 1 hour at 40° and centrifuged. The resulting supernatant was assayed for IL-2 activity. The results are shown in Table V.

Comparative Experiment F

SDS Extraction

Sample K (1 mL) was sonicated three times for 10 seconds. The resulting suspension was centrifuged and the resulting cell pellet was suspended in 0.5 mL of 1% SDS. The resulting combination was incubated for 1 hour at 40° and centrifuged. The resulting supernatant was assayed for IL-2 activity. The results are shown in Table V.

TABLE V

| Example | Comp. Exper. | Extraction Method | IL-2 Activity (units/sample) |
|---|---|---|---|
| 6 | | Acetic Acid 67% | 1,330 |
| | E | SDS (1%) | 1,700 |

TABLE V-continued

| Example | Comp. Exper. | Extraction Method | IL-2 Activity (units/sample) |
|---|---|---|---|
| 7 | | Sonicate, Acetic Acid (67%) | 1,900 |
| | F | Sonicate, SDS (1%) | 660 |

EXAMPLE 8

Extraction of IL-2 from Transformed *E. coli*

MM294 *E. coli* were transformed and grown according to methods similar to those of Example 6. 1950 mL of the resulting culture were harvested by centrifugation and the resulting cell pellet was suspended in 100 mL of 0.05 M Tris and 0.01 M EDTA buffer. The resulting suspension was centrifuged and the resulting cell pellet was resuspended in 100 mL of the same buffer. The resulting suspension was sonicated five times, each for 15 seconds and centrifuged. The resulting pellet was incubated in 80 mL of 67% acetic acid for 1 hour at 40°. The resulting combination was centrifuged and the resulting supernatant was assayed for IL-2 activity. The supernatant was found to have an IL-2 activity of 1,110 units/mL.

EXAMPLES 9–23

Organic Acid Extraction

HB101 *E. coli* were transformed according to a method similar to that of Example 6. The transformed *E. coli* were grown for about 7 hours at 36° in 9.9 L of a minimal medium similar to that of Example 1 containing peptone (3 g/L) and yeast extract (2 g/L) to late logarithmic stage of growth. The *E. coli* were harvested by centrifugation and the resulting cell pellet was suspended in 0.01 M trihydroxyaminomethane hydrochloride, 0.001 M EDTA, 0.15 M sodium chloride (pH 8.0) at 2 to 5 mL per gram of cell pellet. The resulting cell suspension was sonicated for 1 minute at 4° and centrifuged. Equal portions of the resulting cell pellets were individually suspended in acetic acid, formic acid, propionic acid, isobutyric acid and butyric acid at concentrations of 60, 80, and 100 volume percent for a period of at least 30 minutes. The resulting suspensions were centrifuged and the resulting supenatants were assayed for IL-2 activity. The results are shown in Table VI.

TABLE VI

| | Organic Acid Extraction | | |
|---|---|---|---|
| Example | Extraction Method | Protein Extracted (mg/mL) | IL-2 Activity (units/mg) |
| 9 | Formic Acid (60%) | 3.7 | 946 |
| 10 | Formic Acid (80%) | 5.1 | 784 |
| 11 | Formic Acid (100%) | 5.27 | 3,017 |
| 12 | Acetic Acid (60%) | 2.06 | 3,010 |
| 13 | Acetic Acid (80%) | 3.33 | 10,841 |
| 14 | Acetic Acid (100%) | 2.86 | 13,636 |
| 15 | Propionic Acid (60%) | 3.42 | 9,824 |
| 16 | Propionic Acid (80%) | 4.48 | 7,321 |
| 17 | Propionic Acid (100%) | 0.458 | 6,550 |
| 18 | Isobutyric Acid (60%) | 0.209 | 6,220 |
| 19 | Isobutyric Acid (80%) | 0.14 | 1,754 |
| 20 | Isobutyric Acid (100%) | 0.063 | 12,698 |
| 21 | Butyric Acid (60%) | 0.58 | 2,069 |
| 22 | Butyric Acid (80%) | 1.33 | 902 |
| 23 | Butyric Acid (100%) | 0.032 | 56,250 |

What is claimed is:

1. A method for extracting protein produced by procaryotic or eukaryotic cells in the absence of SDS comprising
   (a) contacting the cells with a solution containing from about 50 to about 100 volume percent of an organic acid selected from the group consisting of acetic acid, formic acid, propionic acid, butyric acid, isobutyric acid, and mixtures thereof at a temperature of from about 0° C. to about 40° C. to extract and solubilize protein present in the cells; and
   (b) recovering solubilized protein.

2. A method as defined in claim 1, wherein said protein is produced by procaryotic cells.

3. A method as defined in claim 2, wherein said protein is produced by bacterial cells.

4. A method as defined in claim 3, wherein said protein is produced by transformed *E. coli.*

5. A method as defined in claim 1 wherein the organic acis is acetic acid.

6. A method as defined in claim 5, wherein said cells are contacted with a solution containing from about 60 to about 80 volume percent acetic acid.

7. A method as defined in claim 6, wherein said cells are contacted with a solution containing from about 65 to about 70 volume percent acetic acid.

8. A method as defined in claim 7, wherein said cells are contacted with said solution for from about 30 minutes to about 17 hours.

9. A method as defined in claim 8, wherein said cells are contacted with said solution for from about 50 minutes to about 70 minutes.

10. A method as defined in claim 3, wherein said protein is a lymphokine or a lymphocyte modulator.

11. A method as defined in claim 10, wherein said protein is an interferon or interleukin-2.

12. A method as defined in claim 11, wherein the organic acid is acetic acid, formic acid, propionic acid, butyric acid, isobutyric acid, and mixtures thereof.

13. A method as defined in claim 12, wherein the organic acid is acetic acid.

14. A method as defined in claim 13, wherein said cells are contacted with a solution containing from about 60 to about 80 volume percent acetic acid.

15. A method as defined in claim 14, wherein said cells are contacted with a solution containing from about 65 to about 70 volume percent acetic acid.

16. A method as defined in claim 15, wherein said cells are contacted with said solution for from about 30 minutes to about 17 hours.

17. A method as defined in claim 16, wherein said cells are contacted with said solution for from about 50 minutes to about 70 minutes.

* * * * *